(12) United States Patent
Abitbol et al.

(10) Patent No.: US 9,192,296 B2
(45) Date of Patent: Nov. 24, 2015

(54) MULTIFUNCTIONAL OPHTHALMIC MEASUREMENT SYSTEM

(75) Inventors: Marc Abitbol, Jerusalem (IL); Ian Melnick, Jerusalem (IL); Ran Yam, Jerusalem (IL); Haggai Herman, Givat Shmuel (IL)

(73) Assignee: VISIONIX LTD., Jerusalem (IL)

( * ) Notice: Subject to any disclaimer, the term of this patent is extended or adjusted under 35 U.S.C. 154(b) by 1247 days.

(21) Appl. No.: 12/674,432

(22) PCT Filed: Aug. 21, 2008

(86) PCT No.: PCT/IL2008/001148
§ 371 (c)(1),
(2), (4) Date: Feb. 21, 2010

(87) PCT Pub. No.: WO2009/024981
PCT Pub. Date: Feb. 26, 2009

(65) Prior Publication Data
US 2011/0273669 A1    Nov. 10, 2011

Related U.S. Application Data

(60) Provisional application No. 60/935,594, filed on Aug. 21, 2007.

(51) Int. Cl.
*A61B 3/10*    (2006.01)
*A61B 3/107*   (2006.01)

(52) U.S. Cl.
CPC .............. *A61B 3/107* (2013.01); *A61B 3/1005* (2013.01); *A61B 3/1015* (2013.01)

(58) Field of Classification Search
USPC ......... 351/200, 205, 206, 221, 222, 212, 211, 351/246, 245
See application file for complete search history.

(56) References Cited

U.S. PATENT DOCUMENTS

| | | |
|---|---|---|
| 5,307,097 A | 4/1994 | Baker |
| 5,777,719 A | 7/1998 | Williams |

(Continued)

FOREIGN PATENT DOCUMENTS

| | | |
|---|---|---|
| GB | 2420239 | 5/2006 |
| WO | 02/35452 A1 | 5/2002 |
| WO | WO 02/35452 A1 | 5/2002 |

OTHER PUBLICATIONS

PCT Int'l Search Report and Written Opinion of the ISA, mailed Apr. 21, 2009 in PCT/IL2008/001148.

(Continued)

*Primary Examiner* — Joseph P Martinez
*Assistant Examiner* — Brandi Thomas
(74) *Attorney, Agent, or Firm* — Daniel J. Swirsky; AlphaPatent Associates Ltd.

(57) ABSTRACT

A wavefront measurement system, for measurement of aberrations in the eye, and for measurement of the topography of the cornea of the eye. The system differs from previously available systems in that the wavefront measurement of the eye's aberrations can be performed as a function of eye accommodation. Furthermore, methods for reducing corneal reflection are described. Additionally, the use of a very short focal length Hartman Shack lenslet array enables a very wide range of low order aberrations, up to ±25 diopters, to be measured without any refocusing or motion of the system. Also, methods are described for enabling the presence of defects within the eye to be determined using the aberration measurement system. Another embodiment captures the pupil centering position without any projected illumination pattern being used, so that a subsequent accurate centering and focusing procedure can commence at the initially captured position, thus reducing measurement time.

9 Claims, 10 Drawing Sheets

(56) References Cited

U.S. PATENT DOCUMENTS

| | | | |
|---|---|---|---|
| 5,825,476 | A | 10/1998 | Abitol |
| 5,855,074 | A | 1/1999 | Abitbol |
| 6,130,419 | A | 10/2000 | Neal |
| 6,264,328 | B1 | 7/2001 | Williams |
| 6,460,997 | B1 | 10/2002 | Frey |
| 6,550,917 | B1 | 4/2003 | Neal |
| 6,554,429 | B1 | 4/2003 | Campin |
| 6,565,209 | B2 | 5/2003 | Campin |
| 6,736,509 | B2 | 5/2004 | Martino |
| 6,827,444 | B2 | 12/2004 | Williams |
| 7,036,934 | B1 | 5/2006 | Youssedi |
| 7,146,983 | B1 * | 12/2006 | Hohla et al. ............... 128/898 |
| 7,255,442 | B2 * | 8/2007 | Bucourt et al. ............ 351/221 |
| 2003/0069566 | A1 * | 4/2003 | Williams et al. ............ 606/5 |
| 2003/0120266 | A1 * | 6/2003 | Fujieda ...................... 606/5 |
| 2003/0142271 | A1 * | 7/2003 | Ross et al. ................ 351/212 |
| 2003/0189690 | A1 | 10/2003 | Mihashi et al. |
| 2004/0183997 | A1 | 9/2004 | Suzuki |
| 2004/0239876 | A1 * | 12/2004 | Levine ..................... 351/206 |
| 2005/0007551 | A1 * | 1/2005 | Wakil et al. ............... 351/205 |
| 2006/0132711 | A1 | 6/2006 | Iwanaga |
| 2007/0055222 | A1 * | 3/2007 | Hohla et al. ............... 606/12 |

OTHER PUBLICATIONS

Extended European Search Report, mailed Nov. 27, 2014 in EP 08789820.

* cited by examiner

MULTIFUNCTIONAL OPHTHALMIC MEASUREMENT SYSTEM

CROSS-REFERENCE TO RELATED APPLICATIONS

This application is a U.S. National Phase Application under 35 U.S.C. 371 of PCT International Application No. PCT/IL2008/001148, which has an international filing date of Aug. 21, 2008, and which claims priority to, and the benefit of, U.S. Provisional Patent Application Ser. No. 60/935,594, filed Aug. 21, 2007, the entirety of which is incorporated herein by reference.

The present invention relates to the field of the measurement of optical aberrations in the eye, and the measurement of corneal topography, especially by means of automated equipment.

BACKGROUND OF THE INVENTION

There exist a number of systems for measurement of the aberrations in the visual system of the eye, and for measurement of the topography of the cornea of the eye. In US Published Patent Application No. 2003/0142271, for "Aberration and Corneal Topography Measurement", there is described apparatus for measuring with a single device both the aberrations introduced by an eye and the topography of the cornea of the eye. The method includes determining aberrations within a wavefront created by reflecting a beam off the retina of an eye, determining the corneal topography of the eye from a pattern reflected by the cornea, and directing the beam, wavefront, and reflected pattern using a combiner/separator. The apparatus includes a source for generating the beam for producing the wavefront exiting the eye and a first imaging device for receiving the wavefront, and for determining aberrations using a conventional Hartmann-Shack lenslet array, a projector for projecting the pattern onto the cornea for reflection by the cornea and a second imaging device for receiving the reflected pattern to determine corneal topography, and a combiner/separator for directing the beam, wavefront, and reflected pattern.

In U.S. Pat. No. 7,255,442 for "Device for Measuring Aberrations in an Eye-Type System", there is described a system similar to that described in the above-reference application, but with a number of improvements and in which, inter alia, both the wavefront measurement system and the keratometer measurement system are mounted on one moveable platform.

Other wavefront measurement instruments and methods for measuring ophthalmic aberrations are described in U.S. Pat. Nos. 6,130,419, 6,460,997, 6,550,917, 6,554,429, 6,565,209, 6,736,509, 6,264,328, 5,777,719, 6,827,444, and 7,036,934.

Many of these machines have some drawbacks, whose elimination would make such an instrument more useful and easier to use, and there therefore exists a need for a wavefront measurement system which overcomes at least some of the disadvantages of prior art systems and methods.

The disclosures of each of the publications mentioned in this section and in other sections of the specification, are hereby incorporated by reference, each in its entirety.

SUMMARY OF THE INVENTION

The present disclosure describes a new wavefront measurement system, for measurement of the aberrations in the visual system of the eye, and for measurement of the topography of the cornea of the eye. The system incorporates a number of improvements which facilitate the measurements.

The system differs from previously available systems in that the wavefront analysis assembly and the accommodation measurement module can both move axially independently of each other. This has the advantage that the wavefront measurement of the eye's aberrations can be readily performed as a function of eye accommodation.

The system also differs generally from prior art systems in that, according to another exemplary embodiment, the corneal reflections are reduced in the wavefront measurements by using a combination of a slightly off-axis laser illumination beam, thereby reducing the limitation imposed on the pupil size of the eye that can be measured, and the limited polarization effects generated by the various reflections of the illuminating and reflected beams in their optical paths. The combination of both of these effects results in a simpler and less costly system, with a higher optical throughput, and a wider range of pupil sizes that can be measured.

According to a further example of such systems, the wavefront measurement is performed using a Hartmann Shack lenslet array with a focal length substantially shorter than that of prior art systems, such that the array is disposed very close to the imaging device. This enables a large range to be obtained for the measurement, since even portions of the wavefront with a large slope, arising from large angular deviations from an eye with strong low order aberrations, fall on distinctly defined positions on the imaging device, and can thus be correctly identified. This enables an overall total range of power of up to 50 D (±25 D) to be measured, which covers almost every subject, unlike prior art systems which are more limited in the maximum power that can be measured in a single measurement without the system focus being adjusted.

An additional advantage of such a large measurement range is that it allows a fast initial measurement of the aberrations of the eye to be made with no movement at all of the wavefront measurement assembly. Once the approximate initial measurement has been made, the system can calculate what the approximate system focusing position should be for an eye with such aberrations. The wavefront analyzing system can then be moved directly to that initial focus position, so that the accurate iterative focusing steps needed thereafter to converge onto an accurate focused position to provide accurate aberration measurements, can be performed more rapidly. It therefore becomes significantly quicker for the system control to perform an accurate wavefront measurement using the moveable optical platform.

This arrangement enables the system to perform, according to another exemplary implementation, a fast search for the pupil using only the image of the dark pupil itself, in contrast to typical prior art eye-centering procedures, which initially project an image onto the eye, and then center the eye in the frame using this image. Once the approximate centered and focused position of the eye has been determined approximately, an image is projected onto the pupil, and fine focusing and centering can be continued in the usual manner.

According to yet another system described in this disclosure, a Placido disk pattern is used for centering both the wavefront and the corneal topography measurements. This means that both measurement types share a common centering point, which is the apex of the cornea, and hence no external registration is needed for any subsequent calculations involving both types of measurement. This is in contrast to prior art systems where separate centering axes for these two measurements are generally used, this being intrinsic if separate instruments are used for these two measurements. In such prior art systems, some form of registration procedure is necessary before the two measurements can be correlated to the single eye on which they are performed.

A system and method is also proposed, by which the weak internal surfaces of the cornea and lens can be measured using the Purkinje images of the interfaces generated from a novel Placido disk assembly, in which the ring widths are substantially thinner than those of conventional Placido disks. By this means, and using a preferred sequential illumination of individual rings of the Placido disk, it becomes possible to detect and measure these inner interfaces. Then, together with a measurement of the corneal thickness, which can preferably be performed with a slit lamp or using another angularly off-axis Purkinje image measurement, or an interferometer system, all of the parameters of the front elements of the eye are known.

In other examples of instruments described in this application, there is provided a system for determining the state of accommodation of the subject during the measurement. The system may utilizes the shape of the accommodation curve in order to perform this determination. The method generally involves the use of a target or picture whose image is first located at effective infinity, and which is slowly moved closer to the subject, during which process, the power of the eye may be measured to obtain the accommodation curve. The curve is then inspected for normality of its shape, and the outcome of this inspection is used to determine whether or not the initial eye measurement was of an unaccommodated eye, and it can then be determined if the manifest refraction was measured for a specific accommodation state or at the resting point.

A cataract changes the optical properties of the eye lens such that the lens becomes diffusively reflective in the region of the cataract. According to another novel implementation of the systems of this application, the system can be used for automatic detection of cataracts, using two aspects of the wavefront measurement assembly. The Hartmann Shack camera is used to detect the occurrence of missing or weakened spots from its image, and once detected, their position is determined. The same camera may also be used to detect the presence of a diffusive scattering region, and its position is determined. The instrument tests for spatial correlation between these two positions, which if positive, is a strong indicator of the existence of a cataract in the eye at that position. In addition, a visual camera system can be used to detect localized changes in the image obtained of the eye, and any deviations from regular image intensity noted. The spatial location of such deviations can also be used as a further correlating factor for increasing the reliability of the diagnosis of the eye defect.

According to a further possible implementation, the Hartmann Shack array of spots may be used without additional means to detect the presence of physiological changes in the transmissivity of the eye, which could be attributed to the early stages of formation of a cataract, or to some other eye defect. The sensitivity and resolution of the Hartman Shack measurement in determining small deviations in the wavefront of a collimated beam passing out through the eye is high compared to direct visual inspection, such that it should become possible to detect small transmissive or even refractive changes in the eye before they become of such a magnitude that their effect becomes visible by direct imaging, even at high magnification. This method therefore may assist the physician in detecting the impending development of a cataract or other vision defect in the eye, before such detection becomes possible by direct inspection. Even in circumstances where an earlier detection level is not obtained, the very ability to detect the development of a defect in the eye during the course of a routine refractive test, and without any additional time or cost, provides the instrument of the present invention with an additional significant advantage.

According to another exemplary system, local power mapping can be performed using the Hartmann Shack image to find local irregularities in the eye structure, instead of just the conventional wavefront analysis measurements which determine the aberrations present over the entire surface of the pupil. The eye power is calculated using groups of a limited number of nearest neighbor Hartmann Shack points, such as groups of 4 closest neighbors, or of 9 closest neighbors, rather than using a Zernike fit to the whole surface. This allows for local values of the optical power to be determined. This feature is especially useful for analysis of LASIK presbyopia correction (Laser surgery for formation of a multifocal cornea), for determination of local irregularities in the internal surfaces from the difference between the corneal topography map and the power map, and for Intra Optical Lens multi focal prescriptions.

By using the data generated by the present system, including the corneal radii, the power, cylinder and higher order aberrations of the eye, the corneal thickness, and even the pupil opening by performing the measurements under different illumination conditions, it is possible to build, according to a further aspect of the present invention, an accurate optical model of the eye as a multi-element lens system. The resulting model can then be optimized using a ray-tracing model that takes account of pupil size and field of view. Any suitable optical design program can be used for optimizing the performance of the resulting model. The correction can use either low order aberrations for correction or a combination of low and high orders. The optimization can be based on the spot diagram, MTF, PSF or any other optical metric. Using this optical model, it is possible to prescribe correction lenses accurately based on physical measurements, instead of on the subjective inputs of the subject whose vision is being tested.

The present application thus provides a combination system capable in one instrument, of performing a number of ophthalmic tests which hitherto have required the use of more than one instrument. The presently described systems are able to perform corneal surface topographical mapping, inner layer surface profile mapping, wavefront analysis for eye aberration determination, pachymetry (corneal thickness measurement), ARK (auto-refractometry/keratometry), local power mapping, accommodation determination and pupilometry for measuring pupil dilation response. In addition, such a combination instrument may be used for the early detection of diseases such as Keratoconus and Cataract.

One example implementation involves a system a method of performing measurements on the eye of a subject, the method comprising:

(i) providing a combination wavefront analysis and corneal topography system, the corneal topography system including a visual camera system, (ii) generating visual images of the eye using the camera system, (iii) analyzing the visual images obtained by the camera system to determine the central point of the pupil of the eye, (iv) laterally adjusting the combination wavefront analysis and corneal topography system to co-align their optical axis and this central point of the pupil, (v) projecting an image onto the eye, and (vi) using image processing of the reflection of the projected image from the eye to improve the accuracy of centering of the eye relative to the combination wavefront analysis and corneal topography system.

In such a method, the eye may be illuminated in order to generate the visual images thereof, and the illumination may be dark field illumination. Additionally, in such a method, the step of determining the central point of the pupil of the eye may be performed using image processing routines.

In these exemplary methods, the initial co-alignment of the optical axis with the central point of the pupil enables a quicker achievement of the optimum focus and centralization of the combination wavefront analysis and corneal topography system on the eye, than would be possible without use of this method.

Another exemplary implementation involves a system for detecting the presence of a defect in the eye of a subject, the system comprising:
(i) a light source adapted to provide retinal illumination of the eye, such that part of the retina illumination is reflected from the retina and exits the eye as a wavefront,
(ii) a lenslet array located along an optical path of the wavefront, for receiving the wavefront and for creating a plurality of spot images thereof,
(iii) a detector array that detects the spot images formed by the lenslet array, and
(iv) a computing system for processing images obtained in the system,
wherein the computing system detects any intensity deviation in the plurality of spot images that exceeds a predetermined threshold, and determines its position within the plurality of spot images.

Such a system may also comprise a camera system for providing a visual image of the eye, wherein the computing system may detect within the visual image any region having an intensity deviation from the overall intensity that exceeds a predetermined level, and determines its position within the visual image, and compares the position of intensity deviation in the plurality of spot images with the position of intensity deviation within the visual image and indicates if spatial correlation is detected between the positions of intensity deviation in the plurality of spot images and the visual image.

In such a system, the computing system may further analyze the background illumination between the plurality of spot images formed by the lenslet array, and may then detect any intensity deviation in the background illumination that exceeds a predetermined value, comparing the position of intensity deviation in the background illumination with the position of intensity deviation within the visual image, and indicating if spatial correlation is detected between the positions of intensity deviation in the background illumination and the visual image. This computing system may indicate if spatial correlation is detected between the positions of intensity deviation in all three of the plurality of spot images, the background illumination and the visual image. In either of these systems, the computing system may be either a single system, or a system distributed between various functional modules. The defect may be a cataract.

According to yet another exemplary implementation described in this disclosure, a system is presented for performing a wavefront measurement on the eye of a subject, comprising:
(i) a Shack-Hartman wavefront analysis system analyzing light emerging from the eye after reflection from the retina of the eye, and
(ii) a fixation target unit, adjustable such that the effective distance of the target from the subject can be varied over a range from the subject's near vision to effective infinity, wherein the fixation target unit may be adjustable along the measurement axis independently of the position of the wavefront analysis system along the measurement axis. In such a system, the adjustment of the fixation target unit should enable the wavefront analysis to be performed when the subject's eye is at different states of accommodation. The systems can further comprise at least one beam combining/splitting element, disposed such that the subject can view the fixation target at the same time as the Shack-Hartman wavefront analysis system is analyzing light reflected from the retina of the eye. Additionally, the fixation target may comprise an LCD display. In any of such systems, the accommodation curve of the subject may be obtained and inspected for deviation from a normal curve, the deviation indicating the state of accommodation of the subject during subject was not accommodated during the wavefront measurement.

Another exemplary system for reducing the effects of corneal reflection when making measurements on an eye of a subject is described, the system comprising:
(i) an illuminating beam, at least partly polarized, incident on the eye of the subject, the beam being directed at the eye along an off-axial measurement path such that reflection from the anterior surface of the cornea is directed away from the measurement path because of the curvature of the corneal surface, and
(ii) at least one reflecting surface interposed in the measurement path, the reflecting surface being of such a nature and so aligned that it has different reflectivities to light of different polarization impinging thereon.

In this system, the polarization orientation of the at least partly polarized illuminating beam may be such that light reflected specularly from the cornea of the eye is transmitted less through the at least one reflecting surface, than light diffusively reflected from the retina of the eye, such that the effects of the corneal reflection are reduced. In such a situation, the limited reduction in corneal reflection obtained by the use of the limited off-axis distance mandated by the need of the incident beam to enter the pupil, may be offset by the reduced reflection obtained as a result of the different reflectivities to light of different polarization impinging on the at least one reflecting surface. The at least one reflecting surface may advantageously be aligned in the beam at approximately the Brewster angle.

A further system described herewithin for measuring aberrations introduced by an eye, may comprise:
(i) a light source adapted to provide retinal illumination such that part of the retina illumination is reflected from the retina and exits the eye as a wavefront,
(ii) a lenslet array located along an optical path of the wavefront for receiving the wavefront and for creating a plurality of spot images thereof,
(iii) a detector array that detects the spot images formed by the lenslet array, and
(iv) a calculating module receiving signals from the detector array and adapted to determine the wavefront aberrations from the signals,
wherein the focal length of the lenslets of the array are sufficiently short that the apparatus can cover measurements of low order aberration over a range found in essentially any subject, without need for refocusing.

In this system, the range of low order aberrations found in essentially any subject, may be considered to be within a range of up to $\pm 25$ diopters. Alternatively, it may be in a range of up to $\pm 15$ diopters The calculating module may determine the wavefront aberrations by utilizing the positional displacement of the spot images relative to their position obtained with a collimated light beam incident on the lenslet array.

The focal length of the lenslets of the array may be less than 5 mm, or less than 3 mm., or less than 2 mm. In any event, the focal length of the lenslets of the array may be sufficiently short that the lenslets can be spaced less than 200 micrometers apart without invoking an f-number which degrades the resolution of the Measurements. Alternatively, they may be sufficiently short that the lenslets can be spaced less than 100 micrometers apart without invoking an f-number which degrades the resolution of the measurements. These aberrations measured without refocusing may be used to calculate the expected position of focus for an eye with such aberrations, and to adjust the wavefront measurement assembly such that it is approximately aligned.

Another example implementation involves apparatus for coincident centering of systems for performing ophthalmic measurements on an eye, the apparatus comprising:
(i) a wavefront analysis system, including a Hartman Shack array,
(ii) a corneal topography system, including a visual camera system, and
(iii) an illuminated centering object disposed in front of the eye, such that the illumination from the centering object is reflected from the eye and is imaged by the corneal topography system to define the centralization of the cornea in the corneal topography system,
wherein the wavefront analysis system and the corneal topography system are boresighted on the same optical axis by previous alignment, such that the centering object is effective for ensuring that both the corneal topography images and the wavefront analysis system are commonly centered.

In this apparatus, the images of the centering object may be centered in the corneal topography system by moving the corneal topography system laterally with electric motors. The illuminated centering object may be a generally opaque disc having a concentric pattern which is illuminated so that the corneal topography system can image the reflection of the concentric pattern from the eye surface. The concentric pattern may be illuminated such that its illumination falls on the majority of the corneal surface, such that a corneal topographic measurement of the majority of the corneal surface can be performed. In such a case, the concentric pattern may be illuminated by light emitting diodes emitting in the visible spectrum, in which case, they should illuminate the entire surface of the disc.

As an alternative to the above, the concentric pattern may be illuminated such that only a part of the eye within the pupil aperture is illuminated. The concentric pattern may be illuminated by light emitting diodes emitting outside of the visible spectrum, and then may illuminate a part of the surface of the disc close to its center.

In any of these implementations, the concentric pattern may be a series of concentric rings, such that the centering object is a Placido disc.

Furthermore, such illuminated centering object systems may further comprise a system for obtaining the position of optimum focus of the images of the centering object, by moving the apparatus longitudinally with electric motors until the sharpest reflected images of the centering object are obtained. The sharpest reflected images of the centering object may be obtained by searching for the maximum slope of the images of details of the centering object. The searching may be performed by determining the maximum differences between derivative peaks of the centering object details.

Finally, in these implementations, an important aspect is that the apex of the cornea of the eye may be aligned with the optical axis of the apparatus both for wavefront measurements and for corneal topography measurements.

Additional implementations may involve an exemplary system for measuring the positions of the internal surfaces of an eye, the system comprising:

(i) an illuminated source object disposed such that its illumination is projected onto the eye, the object being generally opaque but having a series of illuminated concentric rings, and
(ii) a detection camera which images the reflection of the illuminated concentric rings in the various surfaces of the eye, wherein the ratio of ring width to width of the opaque regions between rings may be substantially less than 50%.

Such rings of limited width may enable weak internal reflections from the internal surfaces of the eye to be resolved in the presence of a stronger reflection from the cornea anterior surface.

Yet other implementations may involve a system for measuring the thickness of a cornea, comprising:
(i) at least one laser directing its output beam of light onto the corneal surface at an angle of incidence such that the beam of light is reflected from the anterior and posterior corneal surfaces,
(ii) an image detection device, viewing light from the at least one beam reflected from the anterior and posterior corneal surfaces, the light generating interference fringes by interaction of the two reflected light beams, and
(iii) a calculating module for measuring the spacing between the fringes, and for determining corneal thickness from the spacing.

In this system, the at least one laser directing a beam of light onto the corneal surface at an angle of incidence, may be two lasers, each directing a beam of light onto the cornea, the two beams of light being directed onto a region of the cornea at opposite angels of incidence, such that the effects of eye movement on the interference fringe measurement may be reduced.

According to yet another aspect of the present invention, there is provided a method of generating a local power map of an eye comprising the steps of:
(i) illuminating the retina of the eye such that part of the retina illumination is reflected from the retina and exits the eye as a wavefront,
(ii) passing the wavefront through a Hartman Shack array located along an optical path of the wavefront to create a plurality of image spot images thereof,
(iii) detecting the spot images formed by the Hartman Shack array, and
(iv) calculating aberrations of the wavefront from the positions of the detected spots,
wherein the calculating is performed using a group of a small number of localized neighboring spots, such that aberrations of the eye can be determined over a local region corresponding to the group of localized neighboring spots.

In this method, the small number of localized neighboring spots may be either one of four closest neighbor spots or nine closest neighbor spots. In either of these methods described above, aberrations of up to third order can generally be determined. The methods may also comprise the step of comparing the local power map of the eye with a corneal topography map of the eye, such that local irregularities of internal surfaces of the eye can be determined from differences therebetween.

According to further examples described in this application, there is provided a method of generating a model of an eye of a subject, comprising the steps of:
(i) determining a corneal topography map of the eye from a corneal topography measurement,
(ii) determining at least some of the power, cylinder and higher order aberrations of the eye from a wavefront analysis of a wavefront emerging from the eye,
(iii) determining the corneal thickness of the eye from a corneal profiling measurement, (iv) utilizing this data to build an optical model of the eye as a multi-element lens system, and (v) optimization of the model using a ray-tracing model that takes account of pupil size and field of view, wherein the optimized model is used to correct the performance of a lens related to the modeled eye, based on the physical parameters of the eye determined from the model.

In such a method, the optimization can be based on the spot diagram, MTF, PSF or another optical metric. Additionally, the pupil size may be simulated by the optical aperture of the optical model. Subjective data may also be used in combination with the optimized model to correct the performance of the lens.

Finally, the lens related to the modeled eye may be any one of a spectacle lens, a contact lens, an intra optical lens, or an ophthalmic surface generated by refractive laser surgery.

Throughout this application, motion of components or systems in the direction of the optical axis or optical path, namely the Z-direction, may be termed, and may thuswise be claimed, as being in the longitudinal direction, and motions in the X- and Y-directions or in the x-y plane may be termed, and may thuswise be claimed, as being in the lateral direction.

BRIEF DESCRIPTION OF THE DRAWINGS

The presently claimed invention will be understood and appreciated more fully from the following detailed description, taken in conjunction with the drawings in which:

FIG. 12A shows a schematic image from the system visualization camera, detecting the presence of a diffusive scattering region; FIG. 12B shows the corresponding Hartmann Shack image, showing the occurrence of missing or weakened spots; and FIG. 12C shows a schematic image taken on the Hartmann-Shack camera, of a map of the intensity of the spaces between the Hartmann-Shack spots;

DETAILED DESCRIPTION OF PREFERRED EMBODIMENTS

Figure 1:
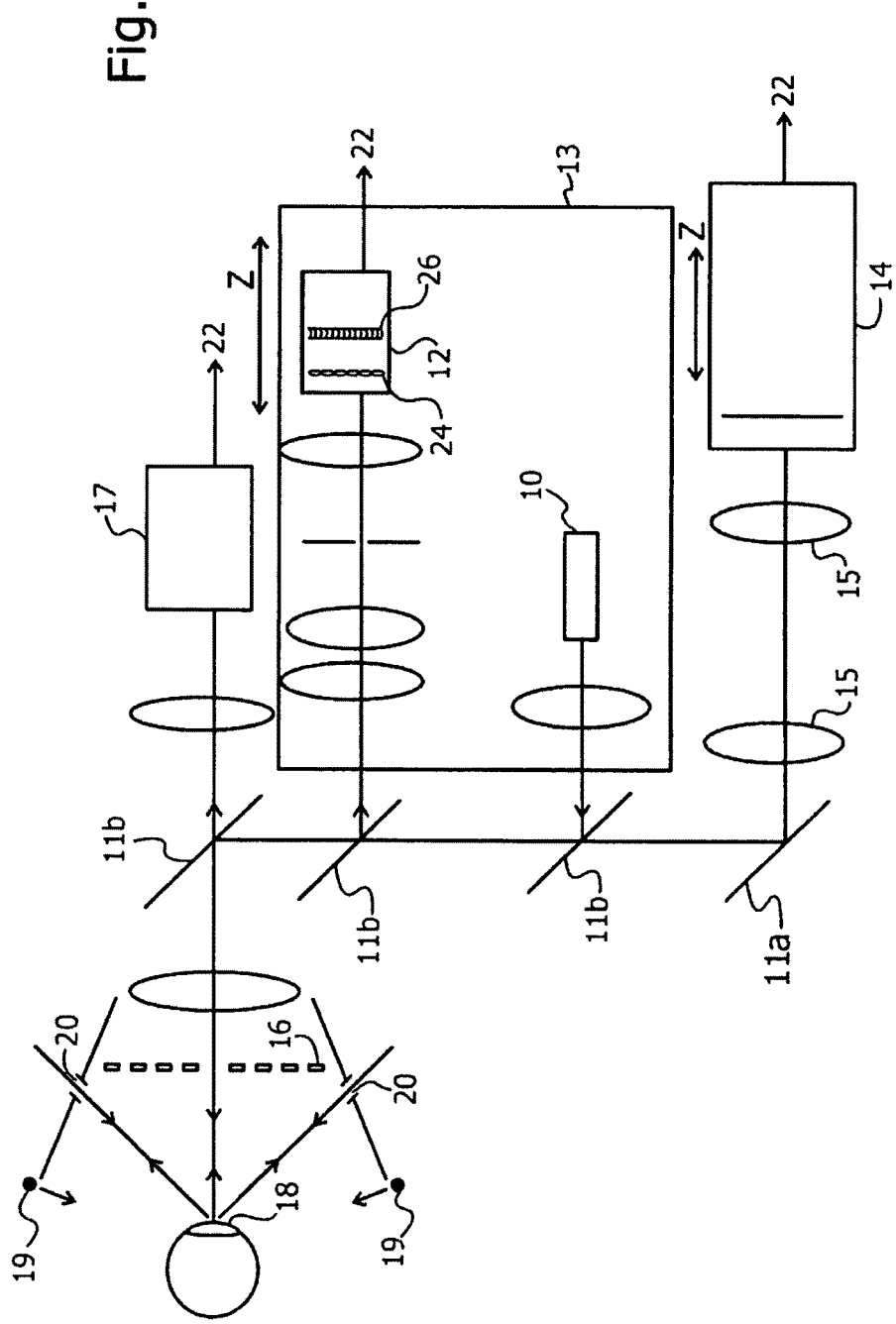
FIG. 1 illustrates schematically a plan view of an exemplary system according to the present claimed invention including both wavefront analysis and corneal topography measurement.

Reference is now made to FIG. 1, which illustrates schematically a plan view of an exemplary wavefront measurement system incorporating some of the novel features described in this application. The system includes a wavefront analysis assembly, as is known in the art, including a laser source 10, mirrors 11a and beam splitters 11b for correctly directing the incident beam to the retina within the subject's eye 18, and for correctly directing the light reflected back from the retina, and a Hartmann-Shack sensor assembly 12 using a lenslet array for providing the image on an imaging device, from which the aberrations of the eye are determined. The wavefront analysis assembly is mounted on its own table 13 which is moveable in the direction of the optical axis between the illumination and the eye, defined as the z-direction. The system also includes a fixation target 14 and associated lenses 15 in order to measure the proper functioning of the accommodation of the eye and to bring the eye focus to a point close to infinity before performing the wavefront measurement.

Additionally, by adjusting the setting of the target 14, it is possible to perform the wavefront measurements with the eye at any desired accommodation, thereby providing more information about the changes in vision with accommodation. The accommodation measurement assembly is mounted separately from the wavefront analysis assembly table 13, such that the z-direction motion of each of these two system components can be performed independently.

A corneal profile measurement system is provided, comprising a Placido disc 16, as is known in the art, or a similar device for illuminating the cornea, and a camera 17 for imaging the reflections of the Placido disc illumination from the cornea 18. From the camera images, the corneal profile can be determined. The entire system can be moved in the x- and y-directions to facilitate correct centering of the eye, and in the z-direction for correct focusing, before taking any measurements.

Finally, a novel system for performing pachymetric measurements on the cornea is included, using laser beams projected at an incident angle which may, for example, be in the region of 45°, through openings 20 on either side of the placido disc casing, as will be further expounded in detail in connection with FIGS. 10 and 11 below.

The wavefront table 13 and the accommodation measurement module 14 are independently moveable in the direction of the optical axis, marked Z, providing a number of advantages to the present system, as will be explained hereinbelow in connection with FIG. 7.

FIG. 1 is meant to show schematically only the various optical components, paths and subsystems of one example of the implementation of an instrument according to the present claimed invention. Only the z-axis subsystem focusing motions are shown in FIG. 1, but it is to be understood that the system also includes x-, y- and z-direction motion for general focusing and centering. Additionally, such standard lenses, dichroic mirrors and other optical components, as used in conventional wavefront analysis arrangements, are not specifically described. Furthermore, it is to be understood that the system should also include electronic signal processing and control systems for interconnecting the various outputs from the detectors and sensors, and the various inputs to table motion motors, focusing motors, and illumination sources, as is well known in the art. To simplify the drawing, these units are not shown in FIG. 1, though their presence is to be understood by the arrows marked 22 leading to the system processing and control units.

The instruments described in this application, as exemplified by that shown in FIG. 1, have a number of additional novel features which may provide significant advantages over prior art instruments, both in use and in accuracy, as follows:

A. Initial Measurement Procedure.

The measurement process begins with an approximate estimate of the eye spherical power. According to this aspect of the present invention, the focal length of the lenslets in the Hartmann Shack array is arranged to be very short, preferably of the order of 5 mm. or less, but not less than the limit where Fresnel diffraction effects become significant, which is typically 2 mm., such that the Hartmann Shack array can be disposed very close to its imaging element. This imaging element can be any suitable array having the required resolution, whether CMOS, CCD or any other device. This close spacing has two related advantages. In the first place, the short focal length results in limited aberration-generated movement of the Hartmann Shack spots from their ordered positions, such that it becomes simpler to keep track of the spot positions even with large aberrations. Secondly, the lenslet diameter and hence the lenslet spacing can be reduced without affecting the f-number of the focusing arrangement. A larger f-number would result in a larger spot size, and hence, lower measurement resolution, so it is important to maintain a small f-number focusing system. The decreased lenslet spacing enables an increased number of lenslets, such that the resolution of the measurement is increased.

This close spacing thus enables a large aberration range to be obtained for the measurement, since even portions of the wavefront with a large slope, arising from large angular deviations from an eye with strong low order aberrations, still fall on distinctly defined positions on the imaging array, and can thus be correctly identified. The use of such a short focal length thus enables an overall total range of the order of up to 50 D to be measured, which covers almost every subject. There is thus an inverse relationship between the aberration range that can be measured and the focal length of the lenslets in the Hartmann Shack array—the shorter the focal length, the larger the aberration range that can be measured.

Prior art systems generally use a longer focal length than those of the present instrument. For instance, in U.S. Pat. No. 7,036,934, a system having a lenslet focal length of 80 mm is mentioned for use with a lenslet array with 800 micron lenslet spacing, or 40 mm for use with a lenslet array with 400 micron lenslet spacing. A large range can be measured with such a long focal length lenslet array, only by use of a comparatively large lenslet spacing, to enable the movement of the neighboring spots to be tracked. However, this would then result in a limited number of spots, and the measurement resolution, and hence overall accuracy would be reduced. Therefore, such a prior art combination of large lenslet spacing and long focal length would generally be more limited than the optical arrangement of the present invention, which provides a good level of accuracy for measurements of large power in a single static measurement without an additional measurement procedure, such as a focusing step through z-motion of the Hartman Shack array.

Since a close lenslet-to-imaging device distance means that very small displacements of the spots on the imaging device need to be measured, in order not to lose spatial sensitivity, the imaging device has to have as small a pixel size as possible, and a device having 1.3 Megapixels or more is preferably used.

In order to maintain the accuracy of the measurement, a high spatial resolution lenslet array should be used, in order to generate sufficient spots to provide good measurement accuracy. A lenslet spacing of 110 microns or less may be advantageous for use in the instruments described in this application.

Additionally, the small spacing/small focal length design of the present instrument results in a significantly less cumbersome instrument than many prior art wavefront measurement devices performing measurements of similar optical parameters of the eye The use of such a large aberration measurement range endows the instruments described here with a significant advantage over prior art instruments, in that it allows a fast initial measurement of the eye to be made without any focusing movement of the wavefront measurement assembly. The short focal length method combined with a high spatial resolution Hartman Shack lenslet array and a high resolution detector is such that it becomes possible to make a measurement of an aberration of up to ±25 D with an accuracy of better than 5% with a one-shot, static measurement, without any focusing steps. This thus enables a quicker convergence for the measurement procedure than prior art instruments which use larger lenslet array-to-detector plane distances, and thus do not have an instantaneous measurement range as large as that achieved by the instruments described herewithin.

The static procedure described above enables the system to determine an approximate value of the low order aberrations over a wide range without an iterative search procedure, such as would be performed by z-axis refocusing. Following this initial capture of the low order eye parameters, generally a sphere and cylinder measurement, the data already obtained on the low order aberrations is used to move the focus to a pre-known position, in order to reduce the spot size of the input laser beam on the retina to a minimum. Without this initial knowledge of the approximate aberrations of the eye, the system would have to perform a number of iterative measurements, changing the Z-axis focus at each iteration in order to converge onto the minimal retinal focused spot size. By using the initially determined, approximate aberration level of the eye, the system can calculate the Z-axis focal setting which provides compensation for these aberrations and which focuses approximately onto the retina, taking the so-far measured aberration into account. From that point on, the measurement continues in the usual manner of iteratively adjusting the z-axis focus to obtain the best focus and to analyze the Hartmann Shack spot array as accurately as possible.

As a result, the light emitted from the focused spot on the retina has optimum collimation on arrival at the Hartmann Shack array, and therefore enables a more accurate measurement to be made. Additionally, this z-direction focusing ensures that the light reflected from the focused spot on the retina can be directed as a collimated beam into the Hartman Shack measurement assembly, thereby compensating for any divergence or convergence imparted to the reflected beam by the power of the eye. This focusing procedure thus effectively compensates for the spherical power of the eye, which for a myopic or a hyperopic eye would generate a larger spot on the retina. Use of an effectively emmetropic eye, which is the result of the z-direction motion, cancels out the effect of any spherical power, thus enabling the higher order aberrations to be measured with greater accuracy.

B. Focusing and Centering Procedure.

According to another example of the instruments and methods described in this application, the focusing and centering procedure may be performed in the following manner, generally using a two stage procedure. The centering algorithm may begin with a search for the pupil, using only the image contrast of the dark pupil itself. This is in contrast to typical prior art eye-centering procedures, which initially project an image onto the eye, and then center the eye in the frame using this image. When only the contrast of the pupil is used, the search can begin at a comparatively large distance from the eye, and the image scanned for a dark region typical of the pupil. Once found, the pupil image contrast itself is used for the initial centering step, which can be performed very quickly. Only when this position has been achieved, is an image projected onto the pupil, and fine focusing and centering performed using this image.

Describing this procedure in more detail, the following steps may be used to provide the optimum measurement accuracy in this application, though it is to be understood that not all of the steps are essential steps for the execution of the method, and the system may be operated and measurements performed with less than all of the steps shown hereinbelow.

1. Images are grabbed from the visualization camera 17, typically at 25 frames per second, to allow rapid performance of the procedure.

2. Dark field illumination is applied to the eye by means of LED's 19 located to the sides of the eye, as shown in FIG. 1. This illumination from the side, by reducing direct back-reflections, shows the pupil boundary very clearly. The image processing routine is then able to detect the black pupil, even if it is far from the properly focused position, and even if only part of the pupil is within the image frame. Dark field illumination simplifies the task of unambiguous detection of the pupil, though it is to be understood that this step may be performed with any suitable illumination, so long as the pupil can be properly identified and centered using that illumination.

3. The image processing routine then searches for the darkest pixel in the image, the image edges being ignored for this step.

4. A search is made for a region around the darkest pixel having a grey level less than a predetermined threshold level (to ensure that the minimum grey level which has been detected really is within the pupil area, and is not simply a dark anomalous spot elsewhere in the ocular image.)

5. The center of this region is then found using any of the commonly known signal processing techniques.

Figure 2:
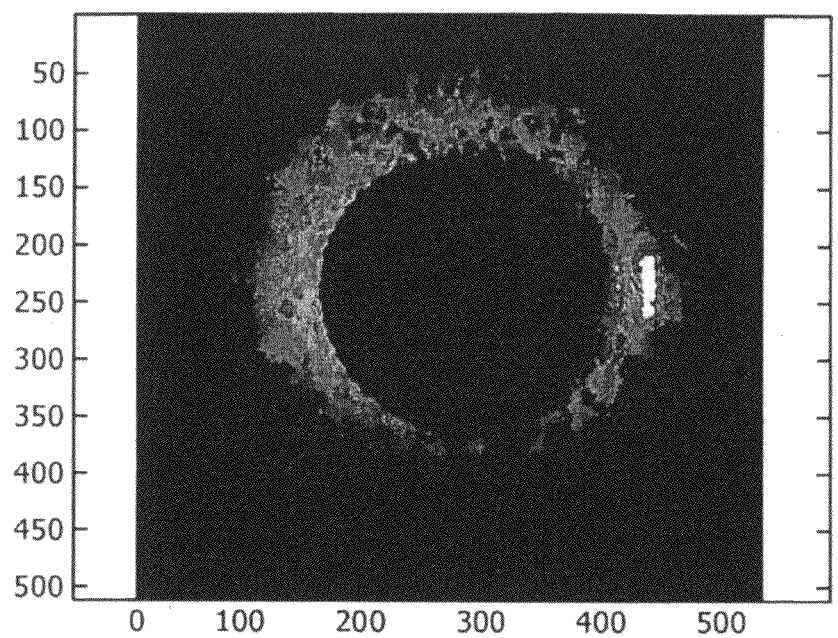
FIG. 2 is a photographic image of the pupil taken using the system of FIG. 1 but with dark field illumination only.

6. The x- and y-motion of the system is activated to bring the center of the region to the center of the image. This is illustrated in FIG. 2, which is a real life photograph of an image of the pupil with the dark field illumination only. The axes of the photograph are marked in pixels of the image, as is also the case for FIGS. 3C and 4.

7. A check is made to confirm that the center of the image is within the darkest pixel, as determined using the above criterion of step 4, and if not, a further iteration is performed.

8. At this point, the initial approximate focusing and centering procedure has been completed, and the procedure may continue using an image projected onto the eye, as is known in the art, which enables an increase in the accuracy of the focusing and centering procedure. The image may be that of a set of Placido rings projected onto the cornea, and the center of the ring, because of the geometry of the reflection of an image from a curved surface, is situated at the corneal vertex position. However, it is to be understood that the instrument and method are not meant to be limited to use of Placido ring images, and that it is within the scope of the present claimed invention to use any other type of image, besides that of Placido rings, which enables the corneal vertex position to be determined.

Figure 3A:
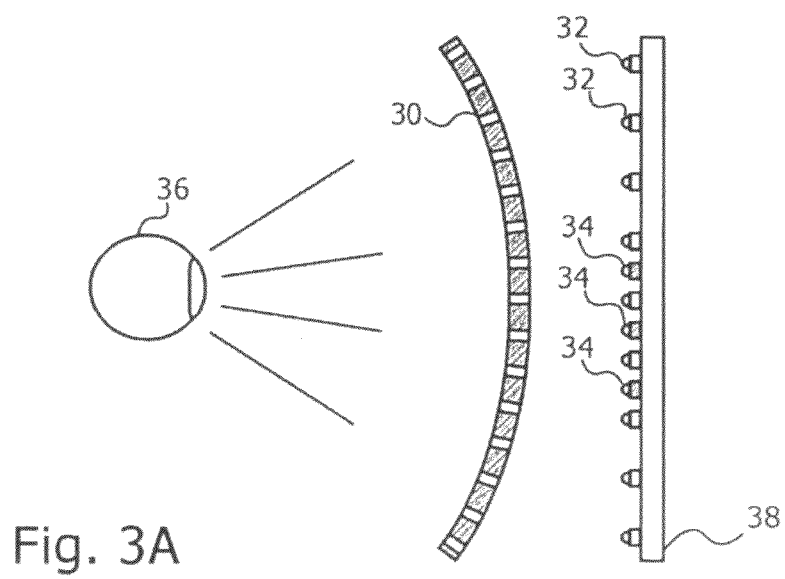
FIG. 3A is a schematic representation of a Placido disc assembly for use according to another implementation of the instrument shown in FIG. 1, showing two different types of illumination.

9. The Placido ring illumination is now activated. Two different modes of illumination may be used, one for the keratometer/corneal topography mode, and another for use when the instrument is in the autorefractometer/wavefront mapping mode. FIG. 3A shows a schematic representation of the Placido disc 30 being used in this implementation, showing the two different types of illumination. During the machine calibration and alignment procedure, both cameras (visualization and wavefront) are aligned together on a single object, such as a set of cross wires. The object is mounted in front of the system on the optical axis and both of the cameras are adjusted until this object is centered on both cameras. The visualization camera may center the cross wire directly in its image frame, while for the wavefront analysis, an artificial eye is used to provide a set of Hartmann Shack points similar to those imaged with a real eye, and the position of the cross wire in front of the eye is determined from a missing spot (or spots) because of the cross wire obstruction. Subsequently, when a given object is centered on the visualization camera it is known that it is also centered on the wavefront camera. Hence centering of the visualization camera on the Placido disk image also centers the wavefront camera on the same image. Therefore, once the Placido ring pattern is centered and aligned for the corneal topography measurements, it is known that the wavefront measurement is also aligned to the same axis, since both measurement types share a common centering point, at the apex of the cornea. This is a significant advantage over prior art measurements, where some external registration procedure is generally needed for calculations involving both types of measurement, in order to relate the axis of reference of the wavefront map to that of the corneal profile map. In the present instrument, both of these maps are centered on the same co-ordinate axis.

10. Referring now again to FIG. 3A, in the corneal topography mode, all of the Placido rings 30 should be illuminated to cover as large a region of the cornea as is necessary. This can readily be achieved in one exemplary implementation, by activating an array of red LED's 32, typically at 650 nm., which are disposed so as to illuminate the entire back surface of the Placido ring pattern. Since pupil dilation does not affect the corneal profile, the use of low cost visible illumination LED's does not affect the corneal topography measurement, though it is to be understood that IR LED's may also be used.

Figure 3B:
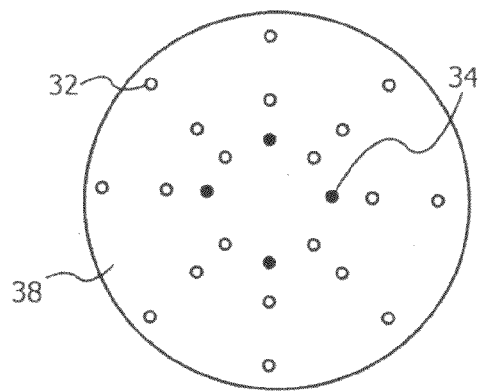
FIG. 3B is a front view of the illuminating board of the Placido disc assembly of FIG. 3A, showing the spatial location of the two different illumination sources.

For use with the wavefront analysis mode, on the other hand, IR LED's 34, emitting at wavelengths invisible to the human eye 36 should be used, so that the pupil size does not change with the illumination, and the effective f-number of the eye lens does not change. A wavelength of 880 nm or 950 nm may be used. A reduced pupil size would result in reduced aberrations being measured, of lower level than those obtained with the normal pupil opening of the eye at normal vision levels due to reduced off-axis and reduced field effects. In the wavefront analysis mode, only the innermost rings need be lit, as shown in FIG. 3A by the location of the IR Led's 34 only in positions close to the axis of the Placido disc, in order to illuminate only the central region of the eye. A single mode of illumination may alternatively be used to illuminate the entire Placido disk, in which case, LED's emitting in the near infra red, outside of the eye's visual response range, should be used, such as with wavelengths 880 nm or 950 nm, in order to avoid the above mentioned effects arising from pupil size. FIG. 3B shows a frontal view of one exemplary illuminating plate 38 for use with the Placido disc 30 described above. The frontal view shows the spatial arrangement of the red LEDs 32 over the whole area of the Placido rings, while the infrared LEDs 34 are disposed such that they only illuminate the central rings.

Figure 3C:
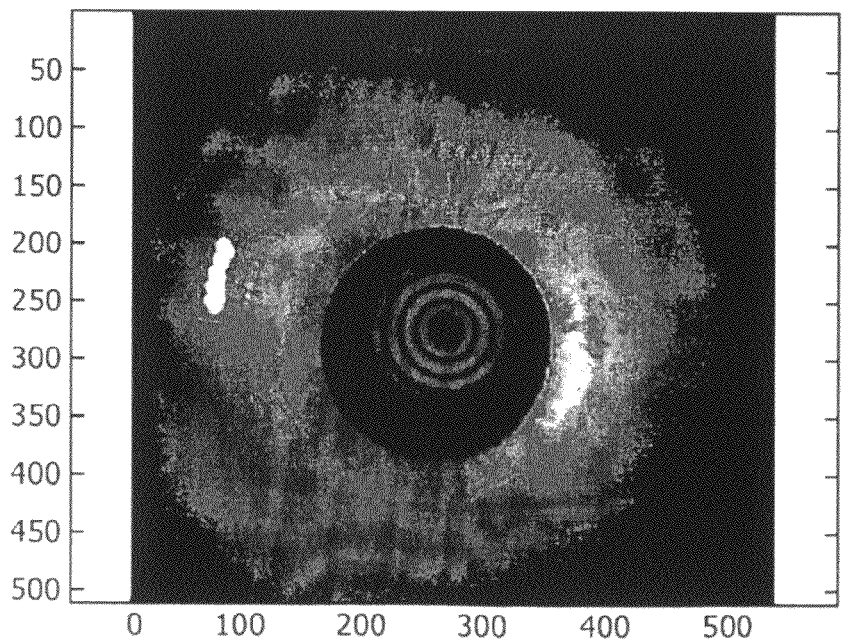
FIG. 3C is a photographic image of a pupil with the Placido rings illuminated for wavefront measurement, showing the central few illuminated rings only.
Figure 3D:
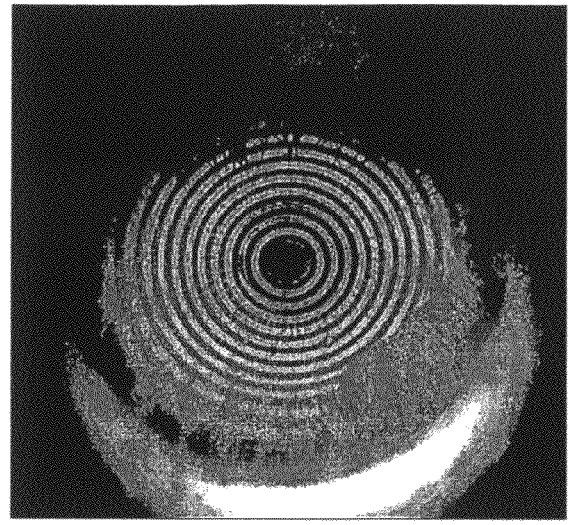
FIG. 3D is a photographic image of the pupil showing the entire Placido ring illumination reflected to enable accurate keratometric and corneal topographic measurements to be made over the entire front surface of the eye.

11. By means of known signal processing procedures, the center of the rings is found, and is brought to the center of the image by means of adjustment of the x- and y-motion motors. The center of the rings is at the corneal apex, may generally be different from the pupil center. The x and y motors are adjusted such that the system moves to bring the corneal apex to the center of the visualization camera image or to any other point that has been defined as the optical axis in the calibration and alignment procedure. This method thus enables use of the same center for both modes of operation, as previously mentioned. FIG. 3C is a typical photograph of the image of a pupil during this measurement, showing the central few illuminated rings. FIG. 3C may be compared with FIG. 3D, which shows an image of the pupil with the entire ring illumination activated to enable accurate keratometric and corneal topographic measurements to be made over the entire front surface of the eye.

Figure 4:
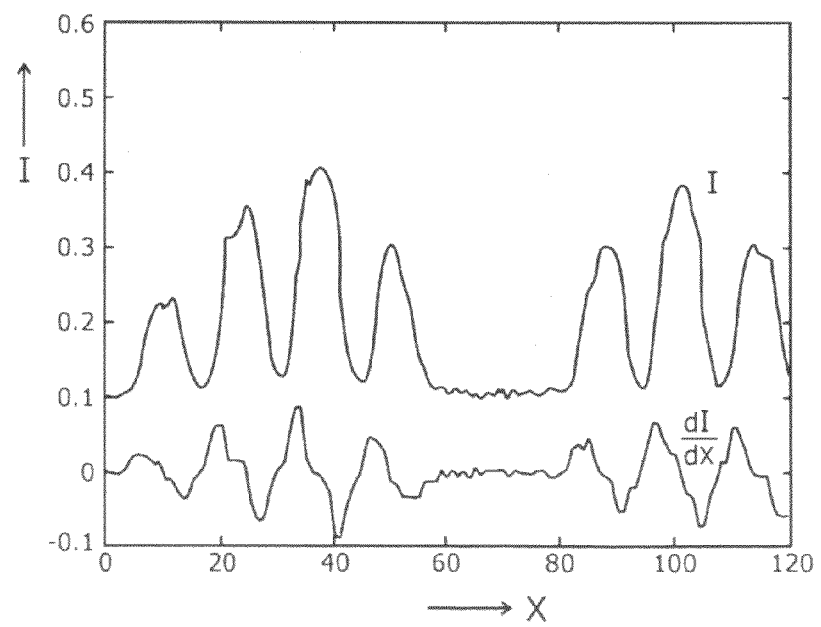
FIG. 4 shows spatial plots across the image of the pupil of a set of rings (upper trace) and the spatial derivatives of their intensity (lower trace)

12. Next, the z-axis focusing motor is operated to search for the best focus position. In the corneal topography mode all the rings can be seen, in the wavefront analysis mode, the central rings only can be seen (if visible light is being used for topography). FIG. 4 illustrates a method by which the optimum focused position of the rings may be most accurately determined. FIG. 4 shows spatial plots across the image of the pupil of a set of rings (upper trace) at a certain z-axis position, and of the spatial derivatives of their intensity (lower trace). Though the plot is conducted in FIG. 4 across the x-axis, it could equally well be performed across the y-axis, or any other radial direction. The units of the abscissa of the graph are image pixels. Looking at the derivative plot, the difference between the derivative peaks is a measure of the sharpness of the rings of the upper plot. In other words, the better the focus, the steeper the slopes of the ring profiles, and the larger the derivatives of these slopes. Thus, when the difference between maximum and minimum derivative values is a maximum, this indicates that the rings are narrowest and sharpest, and therefore, that the focus onto the cornea is optimum. This derivative difference amplitude is therefore a contrast parameter for optimizing the focus. The z axis motor may thus be scanned through the focal region for each image to maximize this contrast parameter, this being at the point of best focus.

13. In practice, a fast scan may first be carried out to find the rough position of the peak of the contrast parameter, and a second slower scan may then be done to find the best focus more accurately.

Once the centering and focusing procedure has been completed, then each separate measurement, of the wavefront analysis and of the corneal profile, can be performed in the knowledge that both of the measurements are performed at the point of optimum focus, and that the measurements are mutually aligned to the same axis, without the need for any external registration device or method.

Once the correct center and focus point is achieved the system can commence the wavefront and/or topography measurements. According to yet another exemplary method of this application, the system can actively track the position of the eye in X, Y, and Z directions, during these measurement procedures. Since typically, a few measurements are taken in order to improve precision, the measurement process is not instantaneous. During this interval, the subject might move his head in any direction, X, Y or Z. According to this new method of operation, the device is programmed to automatically recognize the shift from the optimum centering and focusing point, and to move the relevant x, y or z motors for correction of this movement. In a alternative implementation, the movement can be detected and corrected manually, if the system is so programmed.

C. Corneal Reflection Reduction

Figure 5:
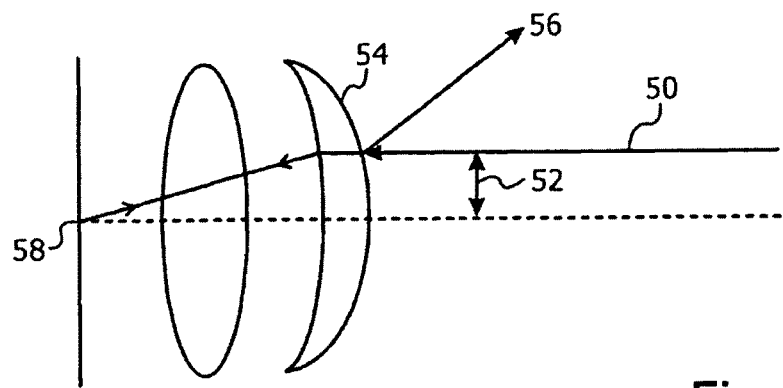
FIG. 5 shows schematically the illumination beam applied to the eye in an off-axis position, for corneal reflection reduction.
Figure 6:
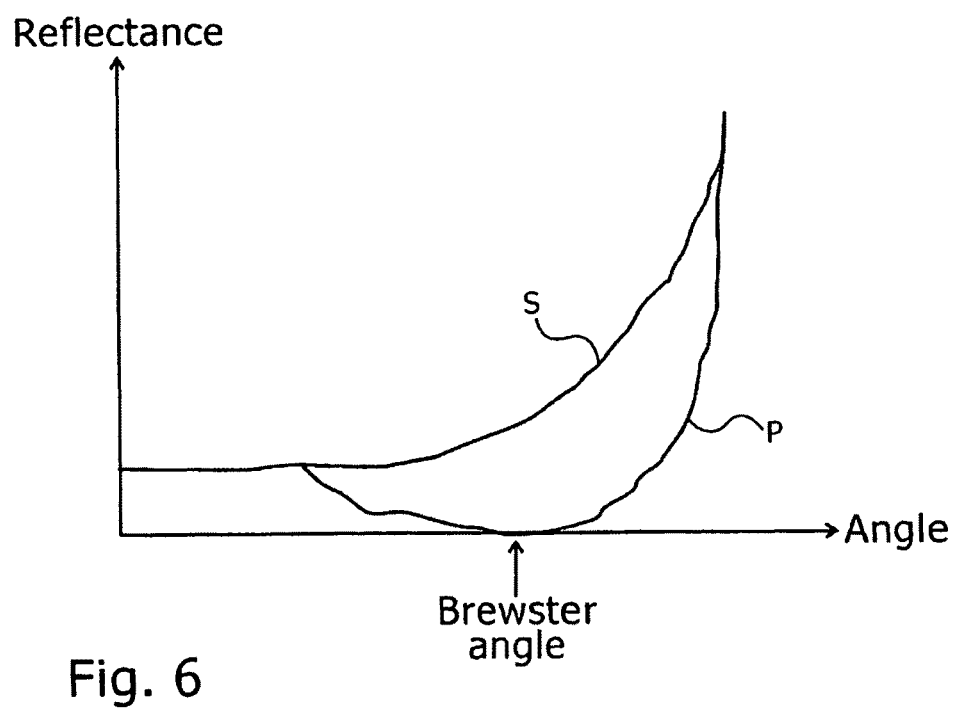
FIG. 6 shows the changes of polarization from a reflecting dielectric surface as the angle of incidence changes.

Reference is now made to FIGS. 5 and 6, which illustrate schematically further optional features of the measurement systems described in this disclosure, by which the effect of corneal reflection is reduced. It is known in the art that in order to reduce the effects of corneal reflection from interfering with the Hartmann Shack measurement image, the illumination beam 50 is applied to the eye in an off-axis position, as shown by the distance marked 52 in FIG. 5. Because of the curvature of the cornea 54, the corneal reflection 56 is directed away from the measurement axis, and does not interfere with the image generation by the light returned from the retina 58. However, this technique introduces a limit on the measurable pupil size—pupils of diameter smaller than the offset 52 cannot be mapped, since the input laser beam will not be able to enter the eye through the pupil.

A second method known in the art is to use polarizing optics to remove the corneal reflection. In such prior art methods, a polarizing optic is inserted into the incident beam path, and because of the rotation of the polarization which takes place on reflection, the reflected beams are blocked by the polarizer and are thus eliminated. However, this solution requires the use of a separate polarization manipulating element, which is an added cost. More importantly, the use of stringent polarization blocking also reduces the wavefront signal strength, since the light diffusely reflected from the retina also undergoes random polarization rotation, and will be partly blocked on its return path through the polarizer optic. Attenuation of 50% of this signal is common, and since the diffuse retinal reflection may generally be weak, it is important to limit the reduction in its intensity as much as possible.

According to this novel feature of the measurement system, use is made of both of these effects in order to combat corneal reflection, by means of a combination of off-axis illumination and partial polarization. A weak polarizer, such as can be found in a typical, coating type, beam splitter, is a reasonably low cost element, and may be implemented as a simple adaptation to the beam splitters 11b, which are used in the instrument shown in FIG. 1. Alternatively and preferably, any of the reflecting surfaces used in the optical path can be used to introduce an element of polarization blocking into the beam. The beam splitters 11b, as shown in FIG. 1 are placed at 45° to the incident beam. This angle is not far from the Brewster angle for typical dielectric materials. For example the Brewster angle for a typical glass material with refractive index 1.5 is 56°. The beam splitters 11*b* used in this implementation therefore behave as partial polarizers.

FIG. 6 shows the effect of reflection from such a reflecting surface, as a function of angle of incidence. At the Brewster angle, the reflected beam is completely S-polarized, and the transmitted beam is partially polarized. At other angles, both beams are partially polarized. The angle of incidence, in combination with the type of coating, can be chosen in order to select the level of polarization to be imparted to the reflected beam.

Operation of this combination method is as follows. The laser source emits a generally polarized beam. Since reflection from the cornea is almost specular, the polarization of the beam reflected therefrom is generally rotated through 90°. The laser is aligned such that this corneal reflected light has generally S-polarization. Consequently, on return through the beam splitters, which are aligned close to the Brewster angle, and/or coated in such a way to allow for larger transmittance of the P polarization in comparison to the S polarization, only a fraction of the S polarized incident light is transmitted, and so its intensity is reduced. On the other hand, the light diffusely reflected from the retina undergoes polarization scrambling, by virtue of the diffuse nature of the retinal reflection, and therefore, its intensity is less affected on reflection in the beam splitters. This method thus reduces the corneally reflected light without affecting the diffusely reflected retinal light to the same extent.

In addition to this partial polarization, which need not appreciably attenuate the measured wavefront signal, off-axis illumination is used, but with a smaller offset than in the prior art arrangement shown in FIG. 5, so that the pupil size is less limited than in the prior art instruments. The result is that the combination of these two effects effectively reduces corneal reflection, but without undue attenuation of the measured signal, without limiting to such an extent, the maximum pupil size that can be measured, and without the need for an additional costly component or components.

D. Accommodation Measurement Technique

In a normal manifest refraction measurement using a sight chart on a distant wall, the eye is usually fairly well corrected for accommodation, or close thereto. On the other hand, a problem arising in the use of any machine-based optometric test is a tendency of the subject to accommodate when looking into a machine, since the subject unconsciously expects to see something within the confines of the machine, i.e. close to the subject. To overcome this phenomenon, optical measurement systems therefore usually incorporate a fixation picture or target, which has an optic in front of it which is adjusted such that the picture appears to be at infinity. When the subject looks at the picture, his eye should become unaccommodated, but this procedure is not always effective, since the subject's expectations may overcome his subjective feelings. Since aberration measurements performed using wavefront analysis vary with the accommodation state of the eye, it is important to be able to determine this state when using a wavefront analysis system such as that described in the present application.

There is therefore now described a novel system for determining the state of accommodation of the subject during the wavefront measurement. The system utilizes the shape of the accommodation curve in order to perform this determination. The method involves the use of a target or picture whose image is first located at effective infinity, and which is slowly moved closer to the subject. The Z-axis motion can be performed by moving the target imaging optics alone, or by moving the target alone, or by moving both the target imaging optics and the target. The change in refraction is measured as the picture moves closer to the subject. As the target picture moves closer to the subject, the power of the eye becomes stronger as the subject accommodates.

Figure 7:
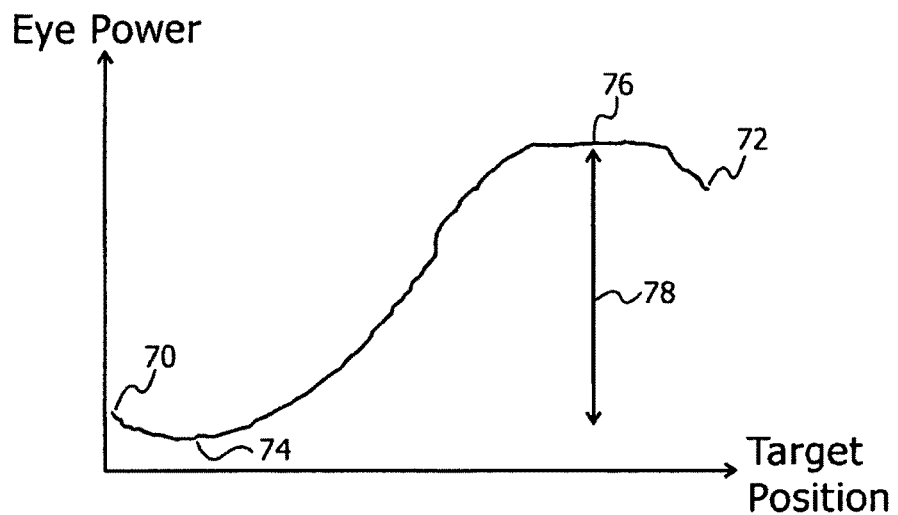
FIG. 7 is an accommodation curve for a typical subject, to illustrate schematically how to determine the state of accommodation of the eye during measurement.

Reference is now made to FIG. 7, which is an accommodation curve for a typical subject, to illustrate schematically how this method is used to determine the state of accommodation of the eye. The spherical power of the eye is plotted as a function of the target distance being viewed, with the far point 70 nominally at effective infinity, at the left hand side of the curve, and the fully accommodated point 72, for near vision being at the right hand side of the curve. The typical accommodation profile for a subject capable of normal accommodation shows a small initial reduction in the spherical power of the eye as the eye moves from the far point 70 at effective infinity towards the resting state 74 with minimum accommodation, and only afterwards does the power increase to the required accommodation state. At the right hand side of the graph, where the target picture is closest, the subject reaches a point 76 at which he can no longer accommodate more strongly. In general, at infinity, the normal subject has some negative accommodation 70, as shown at the left hand side of the graph, and the true rest state 74 is found slightly closer than effective infinity. The difference between the minimum and maximum accommodation is called the accommodation amplitude 78. If such a graph is obtained during this measurement, it is clear that the initial measurement was indeed of an unaccommodated eye, and that the wavefront mapping measurement is able to determine the unaccommodated state of vision of the subject. On the other hand, if the left hand side of the accommodation curve is missing, generally without the initial dip, and the curve shows an elevated value with the accommodation amplitude smaller than normal, this shows that the subject was not able to get to an unaccommodated rest state for the wavefront test, and the wavefront test must be viewed accordingly.

According to further embodiments of this aspect of the invention, the subject's subjective expectations of the expected accommodation distance required of him may be controlled by the use of a variable or interchangeable accommodation target, in order to suit the subject and the measurement to be performed using that target. Thus, for a refractive measurement, where an eye focused at effective infinity is desired, in order to perform the measurement with the eye accommodation in its rest position, a landscape view or similar may typically be chosen, as such an image subconsciously induces the subject to focus to a distance. On the other hand, in order perform a test of the change of the eye's aberrations with accommodation, it is important to ensure that the eye focuses on the image used at the various effective distances at which it is disposed. To induce such definitive focusing, an image with a well defined line pattern is preferably chosen, to induce focusing specifically onto the image. For testing children, the image should preferably be selected to maintain their immediate interest, which suggests the use of children's pictures, or even an animated video sequence. Finally, according to a further exemplary method of this embodiment, a Snellen letter chart series could be used as the fixation image for those applications where a subjective eye test is to be combined in a single instrument with an objective refractive measurement.

According to another implementation of these methods, the fixation target could be an LCD screen which displays images selected according to the use required. Any other type of suitable display screen could also be used. According to another example, a number of different images could be mounted on an image wheel, which is rotated to display the required image to the subject.

This measurement system, having the accommodation measurement and the wavefront analysis modules separately movable parallel to the measurement axes, thus enables the manifest refraction to be determined for any required accommodation state of the subject, or at the subject's resting point, by suitable selection of the target position during the test.

Figure 8:
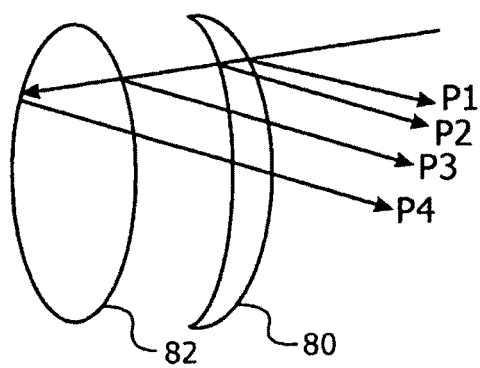
FIG. 8 illustrates schematically a method of measuring the corneal thickness of an eye using a Purkinje type measurement with the system described in the previous drawings.

E. Corneal Thickness and Internal Surface Measurement:

Reference is now made to FIG. 8, which illustrates schematically a method of measuring the corneal thickness of an eye using another application of the system of the present invention. Because of the small differences in refractive index of the intra-ocular fluids, it is difficult to detect the various interface surfaces within the anterior region of the eye, and hence the thicknesses of these regions, i.e. the cornea 80 and the lens 82. According to a further example of the systems described in this application, the Placido ring pattern is activated in a manner which enables the detection of the reflections from all of these surfaces, and hence the determination of the thickness parameters of the cornea 80 and lens 82. These four surfaces of the eye—the anterior and posterior cornea and the anterior and posterior lens surfaces—can be imaged using the four Purkinje images of the rings. Since the first Purkinje image, marked P1 in FIG. 8, from the front surface of the cornea, comes from an interface with a large differential refractive index, it is generally about fifty to a hundred times stronger than the other images, and using a conventional prior art Placido disk system, the reflection P1 therefrom effectively drowns out any of the internal reflections, P2, P3 and P4, rendering them undetectable. Of the internal Purkinje reflections, the most difficult to detect is generally P2, since it is very weak and close to the anterior reflection P1.

In order to overcome these limitations, a Placido disk with rings substantially thinner than those of conventionally used rings may be used to image the internal surfaces. Currently used Placido ring patterns generally have an aspect ratio of 50:50, i.e. the illuminated ring width is the same as the width of the dark spaces between rings. The novel ring structure of this embodiment is such that a much smaller aspect ratio of ring-to-space is used, typically 30%, 15%, or even less. Additionally, the ring system should have the capability of emitting a very intense light level, in order to enable the detection of the reflections from the inner interfaces. The small width of the rings allows a higher image resolution to be obtained than with conventional Placido disk rings, which, for these applications, typically have a width of the order of 1 to 2 mm. For the present system, a Placido ring width of the order of down to 0.1 mm. may advantageously be used, though rings of up to 0.2 mm. or even 0.5 mm width may also provide advantages over previously used Placido rings. A first image with lower intensity is initially generated, in order to find the anterior cornea surface. The low ring intensity is used in order to avoid pixel saturation from the comparatively high level reflection generating image P1. Further images taken with high intensity ring illumination are then used to identify and locate the internal surfaces. According to one exemplary method, each ring is illuminated individually and sequentially to make the image analysis easier. Each separate illuminated ring generates an image incorporating all four of the reflections, and by analyzing the different positions of the ring reflections in each of these sequential images, it is possible to build a model of each of the internal surfaces. According to another example of this method and apparatus, image processing techniques can be used to subtract the reflection generating the image P1, such that P2 can be detected more readily.

Although Placido rings are a commonly used illuminating object for performing topographical mapping measurements of the eye surfaces, it is to be understood that they are only one exemplary method for performing such measurements. According to other embodiments, any form of three dimensional object can be used to plot surface topographies of the eye, including matrices of LED's, or a pixilated LCD array, whereby individual LED's or individual LCD pixels are sequentially illuminated and the reflected image recorded in synchronization with the illumination sequence, such that each illuminated LED or LCD pixel provides another point for the topography mapping. Alternatively, a mechanically chopper rotated in front of an array of illuminated points can be used to generate the sequential illumination required for topographical plotting.

In addition to the measurement of the corneal surface parameters, it is to be understood that this method can also be used for plotting the lens surface topography.

Figure 9:
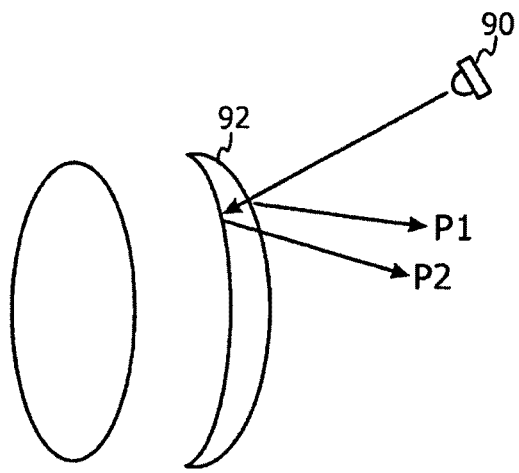
FIG. 9 shows a Purkinje type measurement system to enable the measurement of lens thickness.

The internal surface maps generated do not provide information about the relative positions of those surfaces, and this positional information is necessary to fully characterize the anterior structure of the eye. In particular, the corneal thickness is regarded as an important parameter in this characterization. A separate measurement of the central corneal thickness is thus also generally required. According to another method of this application, this can be achieved by use of a separate Purkinje imaging system. FIG. 9 shows a Purkinje type measurement system to enable this. Light from a single source such as a LED 90 may be directed at a significant angle of incidence onto the cornea 92, and the first two Purkinje reflections, P1 and P2 are imaged on a camera disposed to image these reflections. If the angle of incidence is sufficiently large, the lateral displacement of the LED images in the camera will enable the corneal thickness to be determined from the known angular geometry of the illumination and camera systems.

Figure 10:
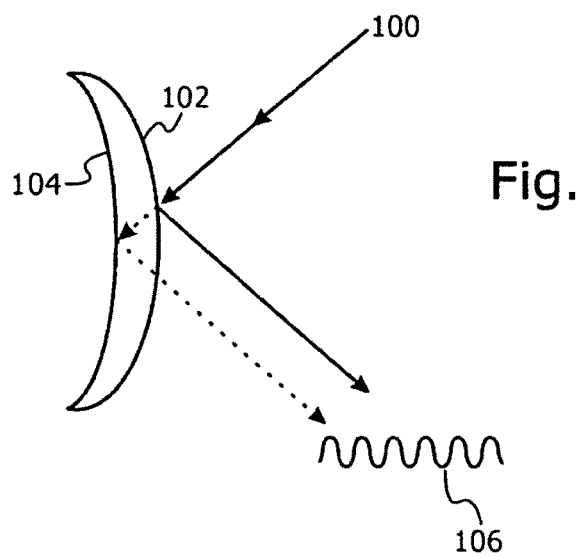
FIG. 10 describe schematically an alternative example of a system for making such pachymetric measurements of the cornea, using fringes generated interferometrically by reflection of a laser beam from the two surfaces of the cornea.
Figure 11:
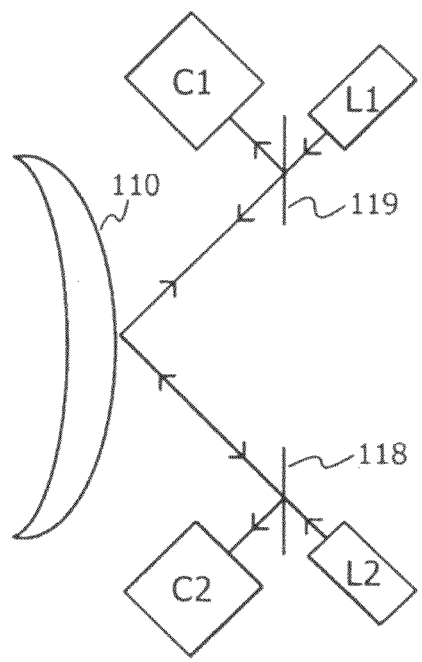
FIG. 11 shows a schematic bidirectional implementation of the system of FIG. 10, to enable the effects of eye tilt to be overcome.

Reference is now made to FIGS. 10 and 11, which describe schematically an alternative example of a system for making such pachymetric measurements of the cornea. In FIG. 10, there is shown a fine collimated laser beam 100 directed at the apex of the cornea, which may conveniently be at an angle in the region of 45°, though other angles may be used, and the reflections from the anterior 102 and posterior 104 corneal surfaces combine to produce a series of interference fringes 106. These fringes may be viewed with an imaging device such as a CCD or CMOS camera. The fringe spacing resulting from the difference in optical path between the anterior and posterior surfaces of the cornea varies with the thickness of the cornea, such that a measure of this fringe spacing enables the corneal thickness to be determined. This measurement can be easily performed using common image processing routines operating on the camera images.

However, since the fringe periodicity is dependent on the differential optical path difference between anterior and posterior surfaces, it is sensitive to the viewing angle of the patient during measurement, since any change in angle of incidence of the laser beam will change the effective thickness through which the beam has to pass before being reflected from the posterior surface. Since it is difficult to maintain the subject's gaze constant during the measurement, it is necessary to provide a system by which changes in the angular direction of the subject's gaze are compensated for. This angular sensitivity can be eliminated by using a bidirectional system of measurement, using two lasers beamed onto the cornea from opposite angles of incidence. This is illustrated in FIG. 11, which is a schematic representation of such a bi-directional measurement system. A first laser L1 directs a measurement beam at the cornea 110, at an angle of incidence of approximately 45° to the eye surface. After reflection in the two surfaces of the cornea (only one reflection is shown in the drawing for simplicity), the reflected beam incorporating the fringe system is reflected by the partial reflector 118, and is detected on the camera C2, where its fringes are measured. A second laser L2, directs a second measurement beam at the cornea 110, generally collinearly with the first reflected beam, and at an angle of incidence of approximately 45° to the eye surface. After reflection in the two surfaces of the cornea, the reflected second beam incorporating its fringe system is reflected by the partial reflector 119, and is detected on the camera C1, where its fringes are measured. The two fringe measurements are then averaged to obtain the result from which the corneal thickness is calculated. Under these conditions, if the axis of the eye moves, the change in angle of incidence of one of the laser beams is compensated for by the complementary change in the angle of incidence of the other beam, and the increase in fringe spacing of one set of fringes is offset by the corresponding decrease in fringe spacing of the other set of fringes.

This method measures the corneal thickness at a single point, typically the centre of the cornea. A Placido disk may be used to ensure the desired eye alignment and focusing and an autorefractometer device such as a Shack-Hartmann wavefront sensor may be used for eye measurement to allow correct target positioning for clarity of vision of the fixation target. Different measurement points on the cornea can be selected by asking the subject to view fixation targets located at different spatial positions. The spatial positions of the fixation targets can be related to the position of impingement of the measurement beams on the cornea. An example of such a unified method of use could be to measure the corneal topography using the Placido disk, followed by selection of various points of interest to the physician on the corneal topography map and measurement of the corneal thickness at those specified positions using the above described system. A fixation target or a single led lamp can be illuminated at the appropriate position, and the subject asked to view the target while the measurement is made.

F. Cataract Detection

The detection of a cataract in a subject's eye is difficult to perform other than by visual inspection by the doctor. A cataract changes the optical properties of the eye lens, such that a small part of the lens becomes diffusively reflecting. A visual inspection shows this as a cloudy, non-transparent region when looking into the eye. However, even such a visual inspection can lead to a faulty diagnosis, since the form of the cloudiness may arise from a number of optical artifacts other than a cataract or other pathological phenomenon.

Figure 12A:
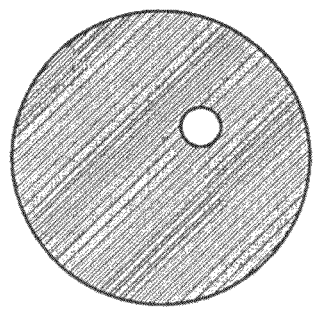
FIGS. 12A to 12C illustrate images provided by the present systems, which enable a method for automatic cataract detection.
Figure 12B:
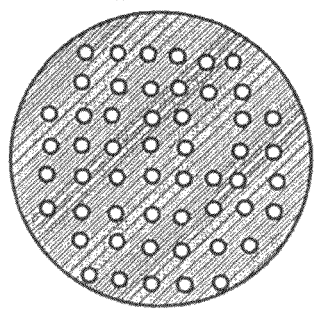
Figure 12C:
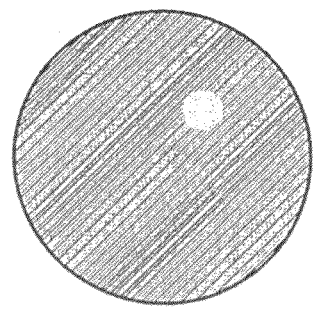

According to a further aspect of the present invention, a method is described whereby instruments described in the present disclosure can be used for the detection of cataracts. The method utilizes a combination of determining the existence of missing information from the retina together with direct inspection of the lens. Reference is made to FIGS. 12A to 12C. FIG. 12A shows the system viewing camera detecting the presence of a diffusive reflecting region when viewing the pupil. The location of the diffusive reflecting region is preferably determined by the image processing software. FIG. 12B shows the corresponding Hartmann Shack camera image, showing the occurrence of missing or weakened spots. Although FIG. 12B shows only a missing spot, it is to be understood that a noticeably weakened spot or spots may also be indicative of an anomaly, such as a cataract. The location of these missing or weakened spots may too be determined by the image processing software. If the deviant features in both of these images occur at essentially the same spatial location in their respective images, then it can be determined as likely that the deviant features arise from a cataract in the eye. Confirmation can be performed by visual inspection by the physician. The existence of spatial correlation between the deviant features can preferably be performed automatically by means of image processing techniques running in the system software. This ability to correlate the positional and optical information from both of these images may enable the provision of machine-based cataract detection, with a level of confidence at least as good as other known detection methods. Although this method has been described in relation to the detection of cataracts, it is to be understood that it is equally well applicable for the detection of other defects within the eye, preferably with an appropriate signal processing routine to interpret the deviant feature seen in the visual image.

According to further implementations of the present method, the Hartmann Shack array of spots, as exemplified by the image of FIG. 12B is used without additional means to detect the presence of physiological changes in the transmissivity of the eye, which could be attributed to the early stages of formation of a cataract, or to some other eye defect, as described in the summary of the invention section of this application.

The Shack-Hartmann light spot image contains more information than just the wavefront of the light emanating from the eye. Regions of the eye with opacity different from the rest of the eye can be detected. Such regions as occurring typically in a cataract have two effects. They scatter light rays that pass through the region, and at the same time, they block the direct path of light from the retina to the detector. The intensity of the Shack-Hartmann light spots on the detector can be mapped and regions of different intensity values can be identified. Similarly the intensity of the spaces between the spots can also be mapped, such as by an image processing subtraction procedure, and regions of different intensity can also be identified. A region containing a cataract will typically reduce the intensity of the Shack-Hartmann light spots and may even remove some spots. At the same time, that region will generally generate an increased level of scattered light, resulting in a higher level of illumination in the background regions between the light spots, as shown in FIG. 12C. A comparison of the two maps in the case of a cataract will show a region where the Shack-Hartmann spot intensity is decreased but the general background level is increased.

There are thus essentially three separate maps, each of which can show information regarding a pathological phenomenon in the eye, such as a cataract. Each of these maps is based on a different physical effect. The visualization camera images direct changes in the light scattered from the eye. The Shack-Hartmann measurement detects missing illumination caused by scattering away of light reflected from the retina. The scattering map is an inverse of the Shack-Hartmann image, in that it shows an increase in diffused background light where the light that would have made up a spot is deflected away from the specific spot direction and into the general background. Correlation of the position of such anomalies in all of three of the maps thus provides a significantly higher level of certainty to the physician's diagnostic conclusions than either one or two of the maps alone could provide.

G. Local Power Mapping.

In a conventional wavefront analysis system, the Hartmann Shack output array of spots is used in order to generate a Zernike polynomial fit to the entire imaged surface of the eye, thus determining the averaged overall sphere or power of the eye, or an averaged higher powered aberration over the whole surface. According to another preferred embodiment of the present invention, instead of looking at the entire surface of the eye, it is possible to perform local power mapping using the Hartmann Shack image to find local irregularities in the eye structure. The local eye power is calculated using the immediately surrounding Hartmann Shack points to define each local region, rather than using a Zernike fit to the whole surface—thus allowing local values to be determined. The use of the detection techniques described in U.S. Pat. No. 5,825,476 for "Apparatus for Mapping Optical Elements", and in U.S. Pat. No. 5,855,074 for "Methods and Apparatus for Measuring and Mapping Ophthalmic Elements", the disclosures of which are incorporated herein in their entirety, facilitate the measurement of such local values of the power of the eye.

Figure 13A:
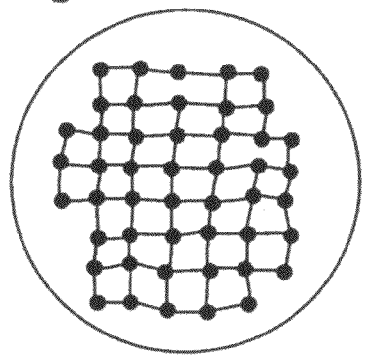
FIGS. 13A to 13C show the manner, according to a further preferred embodiment, by which local power mapping is performed using Hartmann Shack images to find local irregularities in the structure of the eye.
Figure 13B:
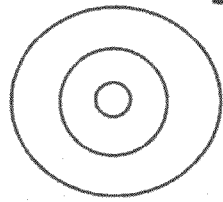
Figure 13C:
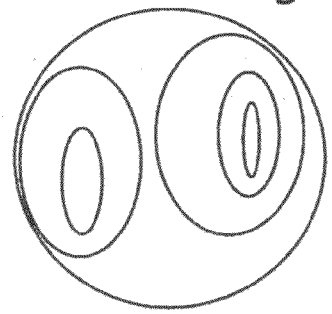

To illustrate this method, reference is made to FIGS. 13A to 13C. Referring to FIG. 13A, the image shows a Hartmann Shack output of the entire eye surface, from which a single value of each aberration is determined for the entire surface, as shown schematically in FIG. 13 B. FIG. 13C, on the other hand shows a local power map, generated by taking individual groups of a small number of neighboring spots, whether the four neighboring spots, or the nine neighboring spots, or more, and calculating the local power from the positions of these small groups of spots. Because of the small number of spots used for each calculation, only the lower order aberrations may readily be determined, possibly up to third order. This method is especially useful for analysis of LASIK presbyopia (laser surgery for formation of a multifocal cornea), for determination of local irregularities in the internal surfaces from the difference between the corneal topography map and the local power map, and for generating Intra Optical Lens multi focal prescriptions.

H. Customized Wavefront Spectacles—Optical Modeling of the Eye.

By use of the various above-mentioned embodiments of the system of the present invention, a number of basic parameters relating to characteristics of the eye and its function can be determined. Thus, from the results of the corneal topography measurements, a complete corneal topography map is known; from the wavefront analysis system, the power, cylinder and higher order aberrations of the eye can be determined; from the corneal profiling measurements, the corneal thickness can be determined. Using all of this data, it is possible to build, according to a further exemplary methods, an accurate optical model of the eye as a multi-element lens system. The model can be further enhanced by performing the wavefront measurements under different illumination conditions, such that the pupil diameter can be changed as desired, this being the optical aperture of the composite lens system. The resulting model can then be optimized using a ray-tracing model that takes account of pupil size and field of view. Any suitable optical design program can be used for optimizing the performance of the resulting model. The correction can use either low order aberrations for correction or a combination of low and high orders. The optimization can be based on the spot diagram, MTF, PSF or any other optical metric.

Once the desired model has been determined, it may become possible to correct the performance of any ophthalmic related lenses, whether spectacle lenses, contact lenses, an IOL, or a surface generated by refractive laser surgery, based not on the subjective outcome of a vision test of the subject, but rather on the physical parameters of the eye whose vision needs correction. Alternatively, the prescription may be based on a combination of both subjective testing, to determine the sphere and cylinder correction needed, and of optical optimization, to determine the higher order corrections needed. The vision correction parameters are defined by calculating the optical correction required for a fully defined lens system—i.e. the fully characterized eye—which has some known areas of reduced optical performance. Such a vision correction procedure can be applied to the prescription of spectacle lenses, of contact lenses, of intra-ocular lenses, or in the planning of corrective laser surgery.

Figure 14:
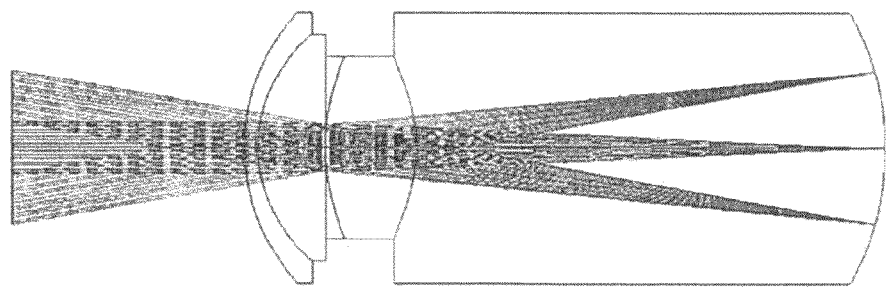
FIGS. 14 and 15 illustrate graphic output data of an optical model of the eye constructed using data obtained from corneal topography, corneal thickness and wavefront analysis measurements, performed with the systems of the present application.
Figure 15:
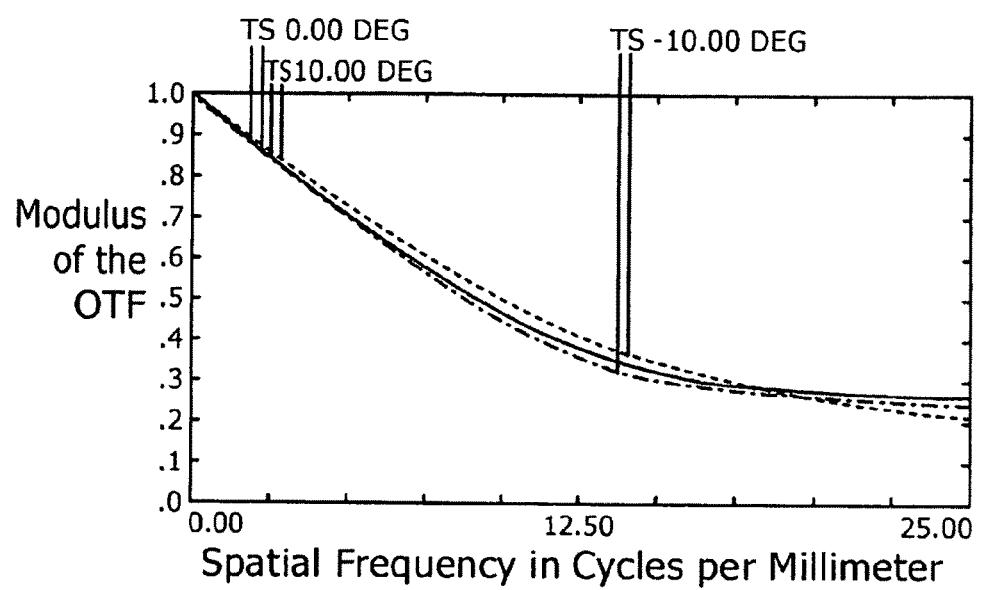

FIGS. 14 and 15 illustrate graphic output data of an optical model of the eye constructed using data obtained from corneal topography, corneal thickness and wavefront analysis measurements performed with the system of the present invention, and of the performance of the eye at various off-axis angular alignments, optimized using the Zemax™ software, with the MTF as the performance parameter.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of performing measurements on the eye of a subject, said method comprising:
   providing a combination system comprising a wavefront analysis system and a corneal topography system that are commonly centered and boresighted to each other on a common optical axis by previous alignment, the corneal topography system including a visual camera system;
   generating visual images including the pupil of said eye using said camera system;
   analyzing said visual images obtained by said camera system to determine the central point of the pupil of said eye;
   laterally adjusting said combination wavefront analysis system and corneal topography system to co-align their common optical axis and the central point of the pupil;
   projecting an image of a centering object onto said eye;
   moving said combination system longitudinally to obtain the position of optimum focus of said image of said centering object; and thereafter using
      (a) image processing of the reflection of said projected image of said centering object from said eye, and
      (b) further lateral adjustment of said combination wavefront analysis system and corneal topography system,
   in order to center the apex of the cornea of said eye relative to said combination wavefront analysis and corneal topography system.

2. A method according to claim 1, and wherein said eye is dark field illuminated in order to generate said visual images thereof.

3. A method according to claim 1, wherein said step of determining the central point of the pupil of said eye is performed using image processing routines.

4. A method according to claim 1, and wherein said initial co-alignment of said optical axis with said central point of said pupil enables quicker achievement of the optimum focus and centralization of said combination wavefront analysis and corneal topography system on said eye, than would be possible without use of this method.

5. A method according to claim 1, wherein said position of optimum focus of said image of said centering object is obtained by moving said combination system longitudinally until the sharpest reflected image of said centering object is obtained.

6. A method according to claim 5, wherein said sharpest reflected images of said centering object are obtained by searching for the maximum slope in the images of details of said centering object.

7. A method according to claim 6, wherein said searching is performed by determining the maximum differences between derivative peaks of the centering object details.

8. A method according to claim 5 and wherein said centering object is a generally opaque disc having a concentric pattern which is illuminated so that said corneal topography system can image the reflection of said concentric pattern from said eye surface.

9. A method according to claim 8 and wherein said concentric pattern is a series of concentric rings, such that said centering object is a Placido disc.

* * * * *